United States Patent
Hirose

(10) Patent No.: US 8,797,545 B2
(45) Date of Patent: Aug. 5, 2014

(54) OPTICAL COHERENCE TOMOGRAPHIC IMAGING APPARATUS AND OPTICAL COHERENCE TOMOGRAPHIC IMAGING METHOD

(75) Inventor: Futoshi Hirose, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 18 days.

(21) Appl. No.: 13/070,060

(22) Filed: Mar. 23, 2011

(65) Prior Publication Data
US 2011/0170115 A1    Jul. 14, 2011

Related U.S. Application Data

(62) Division of application No. 12/493,593, filed on Jun. 29, 2009, now Pat. No. 7,933,024.

(30) Foreign Application Priority Data

Jul. 7, 2008    (JP) .................................. 2008-177108

(51) Int. Cl.
    *G01B 11/02*    (2006.01)
(52) U.S. Cl.
    USPC ......................................................... 356/497
(58) Field of Classification Search
    USPC ................................................. 356/479, 497
    See application file for complete search history.

(56) References Cited

U.S. PATENT DOCUMENTS

| | | | | |
|---|---|---|---|---|
| 7,365,859 B2* | 4/2008 | Yun et al. | ...................... | 356/497 |
| 7,933,024 B2* | 4/2011 | Hirose | ......................... | 356/497 |
| 2006/0055936 A1* | 3/2006 | Yun et al. | ...................... | 356/479 |
| 2007/0263226 A1 | 11/2007 | Kurtz et al. | ................... | 356/492 |
| 2009/0015842 A1* | 1/2009 | Leitgeb et al. | ................ | 356/456 |
| 2009/0244482 A1* | 10/2009 | Elsner et al. | ................. | 351/206 |

FOREIGN PATENT DOCUMENTS

JP    2006/180926    7/2006

* cited by examiner

*Primary Examiner* — Jonathan Hansen
(74) *Attorney, Agent, or Firm* — Fitzpatrick, Cella, Harper & Scinto

(57) ABSTRACT

An optical coherence tomographic imaging apparatus which has a light intensity varying portion provided on a first optical path for guiding a measuring beam to an object for varying an intensity of the measuring beam; an illumination condition varying portion for varying an illumination condition of the measuring beam that has passed through the light intensity varying portion for the object between a first illumination condition in which a center part of the measuring beam is not blocked and a second illumination condition in which the center part of the measuring beam is blocked; and an image forming portion for weighting a first tomographic image acquired in the first illumination condition and a second tomographic image acquired in the second illumination condition and composing the weighted first second tomographic images to form a third tomographic image.

23 Claims, 5 Drawing Sheets

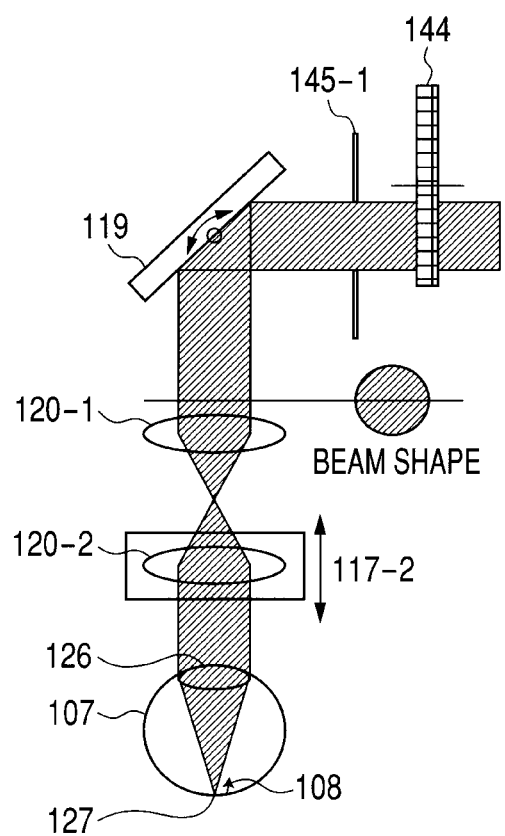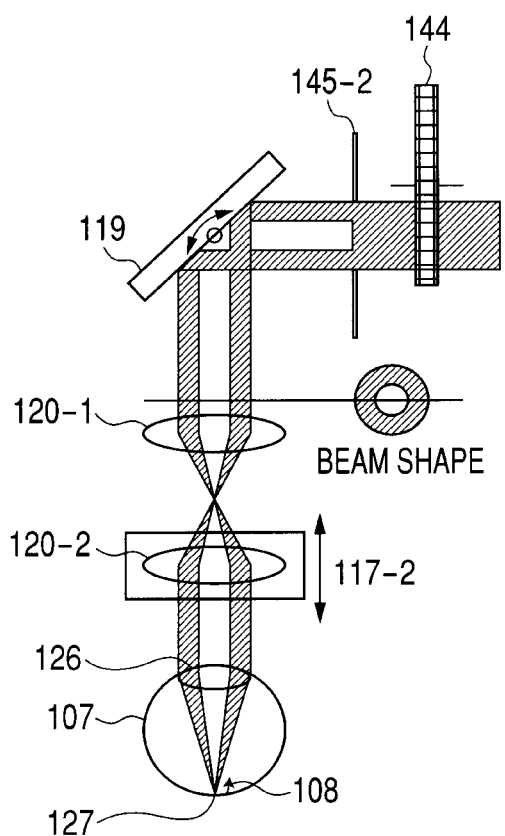

BEAM SHAPE

OPTICAL COHERENCE TOMOGRAPHIC IMAGING APPARATUS AND OPTICAL COHERENCE TOMOGRAPHIC IMAGING METHOD

RELATED APPLICATIONS

This is a divisional of application Ser. No. 12/493,593, filed Jun. 29, 2009, claims benefit of that application under 35 U.S.C. §120, and claims benefit under 35 U.S.C. §119 of Japanese patent application no. 2008-177108, filed Jul. 7, 2008. The entire contents of each of the mentioned prior applications are incorporated herein by reference.

BACKGROUND OF THE INVENTION

1. Field of the Invention

The present invention relates to an optical coherence tomographic imaging apparatus and an optical coherence tomographic imaging method, and more particularly, to an optical coherence tomographic imaging apparatus and an optical coherence tomographic imaging method which are used for ophthalmologic diagnosis and treatment.

2. Description of the Related Art

An optical tomographic imaging apparatus for optical coherence tomography (OCT) using multi-wavelength optical coherence (hereinafter referred to as OCT apparatus) is capable of acquiring a tomographic image of a retina at a fundus of an eye to be inspected at high resolution, and is widely used for ophthalmologic diagnosis of the retina.

The OCT apparatus is an apparatus for irradiating the fundus of an eye to be inspected with a measuring beam which is a low-coherent beam to obtain interference light between backscattered light from the fundus and a reference beam.

There is disclosed in Japanese Patent Application Laid-Open No. 2006-180926 an operation microscope for imaging the same field of view with two illumination conditions (bright field and dark field) and displaying an image obtained by composing a chroma-key-processed dark field image on a bright field image.

According to such operation microscope, a visible light image is acquired in the bright field condition and a fluorescent image is acquired in the dark field condition. The images acquired in the bright field condition and the dark field condition can be treated as a single image. Therefore, a position of an affected part which generates fluorescence may be accurately determined.

The intensity of the backscattered light for forming the tomographic image depends on the incident angle of the measuring beam on the retina. Therefore, there is a case where it is difficult to measure a target layer or part of the retina with high sensitivity.

This is because, though high-sensitive measurement may be achieved in a case where the measuring beam is substantially perpendicularly incident on the target layer of the retina, high-sensitive measurement is not achieved in a case where the measuring beam is incident on the target layer at an angle which is not substantially perpendicular. In such a case as described above, sensitivity is varied in a tomographic image, with the result that the contrast of the tomographic image becomes lower.

If the intensity of the measuring beam is increased for the case where the contrast of the tomographic image is low, the thermal noise of a light receiving element relatively reduces, and hence the contrast of the tomographic image is improved.

However, in the case where the retina is to be imaged, there is a limit on the intensity of a measuring beam in view of the influence on the retina. Thus, it is not better to increase the intensity of the measuring beam.

In Japanese Patent Application Laid-Open No. 2006-180926, measures against a problem with respect to the contrast of the tomographic image are not taken into account.

SUMMARY OF THE INVENTION

The present invention has been made in view of the above-mentioned problem. Therefore, it is an object of the present invention to provide an optical coherence tomographic imaging apparatus and an optical coherence tomographic imaging method which are capable of acquiring a tomographic image with high contrast.

According to a first aspect of the present invention, there is provided an optical coherence tomographic imaging apparatus in which a beam from a light source is split into a measuring beam and a reference beam to guide the measuring beam to an object and to guide the reference beam to a reference mirror; and a tomographic image of the object is acquired based on a return beam of the measuring beam which is reflected or scattered by the object and the reference beam reflected by the reference minor, the optical coherence tomographic imaging apparatus comprising:

a light intensity varying portion for varying an intensity of the measuring beam, the light intensity varying portion being provided on a first optical path for guiding the measuring beam to the object;

an illumination condition varying portion for varying an illumination condition of the measuring beam that has passed through the light intensity varying portion for the object between a first illumination condition in which a center part of the measuring beam is not blocked and a second illumination condition in which the center part of the measuring beam is blocked; and an image forming portion for weighting a first tomographic image acquired in the first illumination condition in which the center part of the measuring beam is not blocked and a second tomographic image acquired in the second illumination condition in which the center part of the measuring beam is blocked and composing the weighted first tomographic image and the weighted second tomographic image to thereby form a third tomographic image.

Further, according to a second aspect of the present invention, there is provided an optical coherence tomographic imaging method in which:

a beam from a light source is split into a measuring beam and a reference beam to guide the measuring beam to an object and to guide the reference beam to a reference mirror;

an optical waveform obtained by interference between a return beam of the measuring beam which is reflected or scattered by the object and the reference beam reflected by the reference minor is converted into an electrical signal by an opto-electric conversion circuit; and a tomographic image of the object is acquired based on the electrical signal, the optical coherence tomographic imaging method comprising:

a first step of varying an intensity of the measuring beam by a light intensity varying unit provided on an optical path for guiding the measuring beam to the object;

a second step of obtaining an electrical signal for acquiring a first tomographic image in a first illumination condition in which a center part of the measuring beam is not blocked using an illumination condition varying portion including an exchangeable aperture for varying an illumination condition of the measuring beam that has passed through the light intensity varying unit for the object between the first illumination condition in which the center part of the measuring beam is not blocked and a second illumination condition in which the center part of the measuring beam is blocked, to;

a third step of obtaining an electrical signal for acquiring a second tomographic image in the second illumination condition in which the center part of the measuring beam is blocked using the illumination condition varying portion; and a fourth step of weighting the electrical signal for acquiring the first tomographic image and the electrical signal for acquiring the second tomographic image, which are different in amplitude from each other, and adding the electrical signal for acquiring the first tomographic image and the electrical signal for acquiring the second tomographic image through operation to form a third tomographic image with a contrast adjusted.

Further, according to a third aspect of the present invention, there is provided a computer-readable recording medium which stores a program for causing a computer to execute the optical coherence tomographic imaging method.

Further, according to a fourth aspect of the present invention, there is provided a program for causing a computer to execute the optical coherence tomographic imaging method.

Further, according to a fifth aspect of the present invention, there is provided an optical coherence tomographic imaging method, comprising:

irradiating a fundus with a first measuring beam having an illumination condition in which a beam center part is not blocked at a first light intensity;

acquiring a first tomographic image based on a return beam of the first measuring beam from the fundus;

changing the illumination condition by the illumination condition varying portion to change the first measuring beam to a second measuring beam having an illumination condition in which the beam center part is blocked;

adjusting the second measuring beam to a second light intensity by the light intensity varying portion so as to enter the fundus at the first light intensity;

irradiating the fundus with the second measuring beam at the second light intensity;

acquiring a second tomographic image based on a return beam of the second measuring beam from the fundus;

weighting the first tomographic image and the second tomographic image; and composing the weighted first tomographic image and the weighted second tomographic image to acquire a third tomographic image.

According to the present invention, it is possible to realize the optical coherence tomographic imaging apparatus and the optical coherence tomographic imaging method which are capable of acquiring the tomographic image with high contrast.

Further features of the present invention become apparent from the following description of exemplary embodiments with reference to the attached drawings.

BRIEF DESCRIPTION OF THE DRAWINGS

FIGS. 3A and 3B are explanatory views illustrating an image forming method using the OCT apparatus according to Example 1 of the present invention, in which FIGS. 3A and 3B are explanatory views illustrating a measurement optical system of the OCT apparatus.

FIGS. 4A, 4B, 4C, 4D and 4E are explanatory views illustrating an image forming method using the OCT apparatus according to Example 1 of the present invention, in which FIGS. 4A to 4C are schematic views illustrating first, second, and third tomographic images, FIG. 4D is an explanatory flowchart illustrating a method of forming the third tomographic image based on the first and second tomographic images, and FIG. 4E illustrates a beam shape in a case where a quadrupole aperture is used.

DESCRIPTION OF THE EMBODIMENTS

Figure 1A:
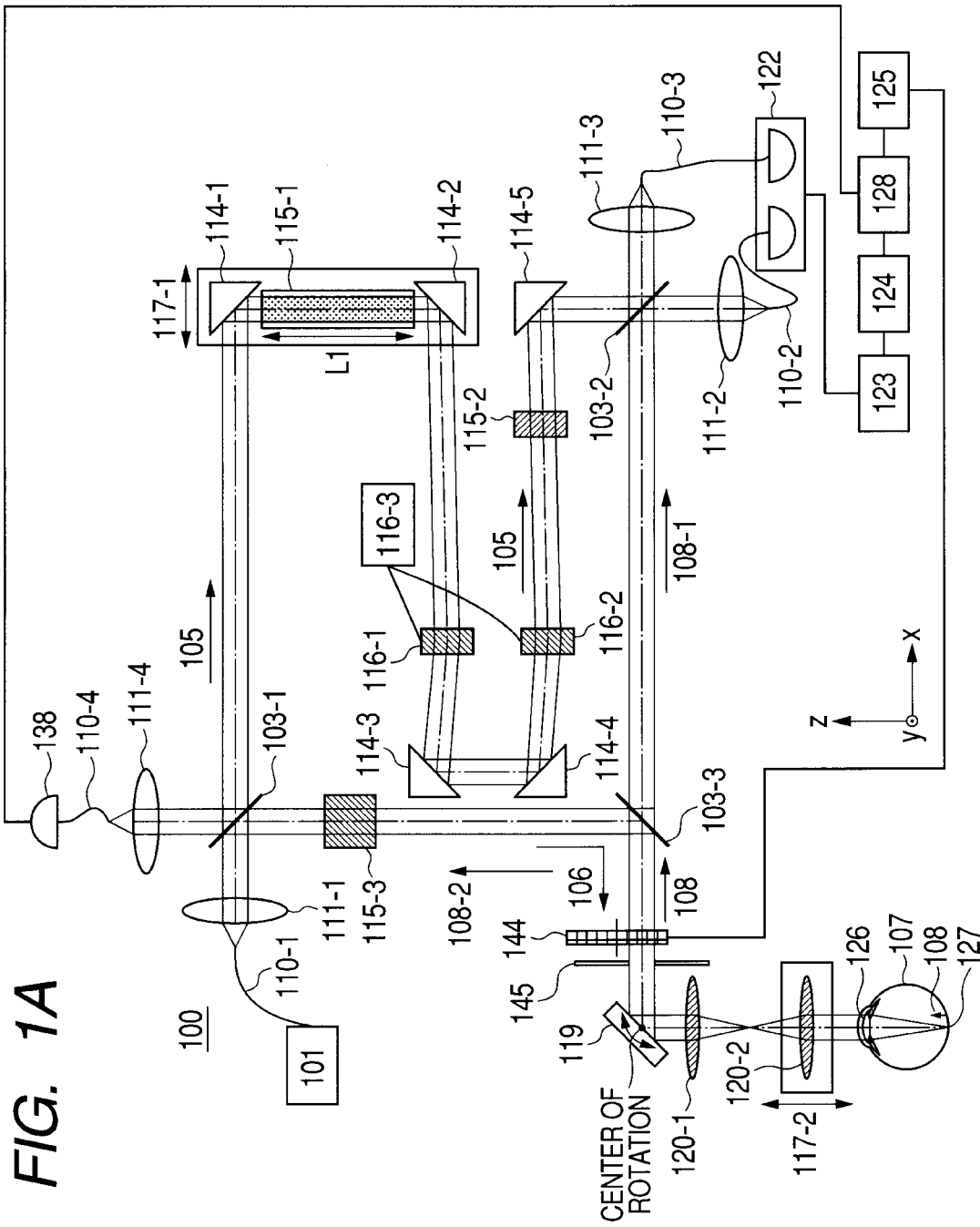
FIGS. 1A and 1B are explanatory views illustrating schematic structures of the entire optical systems of OCT apparatuses according to Example 1 and Example 2 of the present invention.

An optical tomographic imaging apparatus (or optical coherence tomographic imaging apparatus (OCT apparatus)) and an optical tomographic (or optical coherence tomographic) imaging method according to an embodiment of the present invention are described below with reference to FIGS. 1A and 1B, 3A and 3B, and 4.

As described above, the intensity of the backscattered light for forming the tomographic image depends on the incident angle of the measuring beam on a sample, with the result that there is the problem that the contrast of the tomographic image becomes lower.

In order to solve the above-mentioned problem, the optical tomographic imaging apparatus (OCT apparatus) and the optical tomographic imaging method in this embodiment are constructed as in the following items (1) to (10).

(1) In an optical tomographic imaging apparatus 100 according to this embodiment, a beam from a light source 101 is split into a measuring beam 106 and a reference beam 105. The measuring beam 106 is guided to an object 107. The reference beam 105 is guided to reference minors 114-1 to 114-5. A return beam 108 of the measuring beam 106 which is reflected or scattered by the object 107 and the reference beam 105 reflected on the reference mirrors 114-1 to 114-5 are used to acquire a tomographic image of the object 107. The optical tomographic imaging apparatus 100 includes a light intensity varying unit 144 for varying an intensity of the measuring beam 106 and an illumination condition varying unit 145 for varying an illumination condition of the measuring beam 106 for the object 107.

The light intensity varying unit 144 is provided on an optical path for guiding the measuring beam 106 to the object 107, to vary the intensity of the measuring beam.

The illumination condition varying unit 145 is provided to vary the illumination condition of the measuring beam 106 that has passed through the light intensity varying unit 144 for the object 107, between an illumination condition in which a center part of the measuring beam 106 is not blocked and an illumination condition in which the center part thereof is blocked.

The illumination condition varying unit 145 composes a first tomographic image acquired in the condition in which the center part of the measuring beam 106 is not blocked on a second tomographic image acquired in the condition in which the center part of the measuring beam 106 is blocked.

A third tomographic image whose contrast is high is formed by the composition.

Therefore, even when the illumination condition is varied to change the intensity of the measuring beam 106, the intensity of the measuring beam 106 can be maintained constant. As a result, the contrast of the acquired tomographic image can be maintained.

(2) According to the optical tomographic imaging apparatus 100 in this embodiment, in order to vary the illumination condition, the illumination condition varying unit 145 may include:

a circular aperture 145-1 for obtaining the illumination condition in which the center part of the measuring beam 106 is not blocked; and a ring aperture 145-2 for obtaining the illumination condition in which the center part of the measuring beam 106 is blocked.

Therefore, the measuring beam 106 is formed into a ring shape to realize so-called zone illumination, and hence the object 107 may be obliquely irradiated with the measuring beam 106.

In this case, an acquired tomographic image is formed based on only the return beam 108 generated when the object 107 is obliquely irradiated with the measuring beam 106.

As a result, the contrast of a layer of a retina 127 which is not substantially perpendicular to the optical axis of the measuring beam 106 becomes relatively high, and hence variation in contrast on a tomographic image can be reduced.

(3) According to the optical tomographic imaging apparatus 100 in this embodiment, in order to vary the illumination condition, the illumination condition varying unit 145 may include:

the circular aperture 145-1 for obtaining the illumination condition in which the center part of the measuring beam 106 is not blocked; and an aperture having multiple openings, for obtaining the illumination condition in which the center part of the measuring beam 106 is blocked.

Therefore, the measuring beam 106 is formed into multiple measuring beams to realize, for example, quadrupole illumination, and hence the object 107 may be obliquely irradiated with the measuring beam 106. In this case, an acquired tomographic image is formed based on only the return beam 108 generated when the object 107 is obliquely irradiated with the measuring beam 106.

As a result, the contrast of a layer of the retina 127 which is not substantially perpendicular to the optical axis of the measuring beam 106 becomes relatively high, and hence variation in contrast on a tomographic image can be reduced.

(4) According to the optical tomographic imaging apparatus 100 in this embodiment, the apertures described above can be mutually exchangeable.

Therefore, when the illumination condition is to be changed, the apertures may be exchanged to realize a necessary illumination condition. For example, the ring apertures 145-2 having various diameters or a quadrupole aperture may be used.

As a result, a suitable illumination condition can be selected for every object 107 to acquire an appropriate tomographic image.

(5) According to the optical tomographic imaging apparatus 100 in this embodiment, the light intensity varying unit 144 may be provided to control the intensity of the measuring beam 106 by a control unit. Therefore, the intensity of the measuring beam 106 can be automatically maintained constant. As a result, the contrast of the acquired tomographic image can be automatically maintained.

(6) According to the optical tomographic imaging apparatus 100 in this embodiment, the light intensity varying unit 144 may be a neutral density filter.

Therefore, the intensity of the measuring beam 106 may be easily and stably varied.

(7) The optical tomographic imaging apparatus 100 according to this embodiment may further include:

an opto-electric conversion circuit 122 which converts, into an electrical signal, an optical waveform obtained by interference between the return beam 108 and the reference beam 105 in a case where the return beam 108 and the reference beam 105 are used;

an A/D converter 128 which converts, into a digital value, the electrical signal obtained by the opto-electric conversion circuit 122; and an amplification control unit for controlling amplification of the electrical signal converted by the A/D converter 128.

Therefore, the electrical signal may be appropriately converted into the digital value according to the amplitude of the electrical signal. As a result, a high-precision tomographic image may be obtained.

(8) According to the optical tomographic imaging apparatus 100 in this embodiment, at least one of:

an optical path for guiding the beam from the light source 101 to an optical path on which the beam is split into the measuring beam 106 and the reference beam 105;

the optical path for guiding the measuring beam 106 to the object 107;

an optical path for guiding the return beam 108 to the opto-electric conversion circuit 122; and an optical path for guiding the reference beam 105 to the opto-electric conversion circuit 122 may be of an optical fiber. Therefore, the optical tomographic imaging apparatus 100 which is small in size and stable may be realized.

(9) According to the optical tomographic imaging method in this embodiment, the beam from the light source 101 is split into the measuring beam 106 and the reference beam 105. The measuring beam 106 is guided to the object 107. The reference beam 105 is guided to the reference mirrors 114-1 to 114-5. The return beam 108 of the measuring beam 106 which is reflected or scattered by the object 107 and the reference beam reflected by the reference minors 114-1 to 114-5 are used for interference between the return beam 108 and the reference beam 105, thereby obtaining the optical waveform. The optical waveform is converted into the electrical signal by the opto-electric conversion circuit 122. The tomographic image of the object 107 is formed based on the electrical signal.

The optical tomographic imaging method may include the following first to fourth steps.

In the first step, the light intensity varying unit 144 provided on the optical path for guiding the measuring beam 106 to the object 107 is used to vary the intensity of the measuring beam 106.

In the second step, the illumination condition varying unit 145 including the exchangeable aperture is used to vary the illumination condition of the measuring beam 106 that has passed through the light intensity varying unit 144 for the object 107 between the illumination condition in which the center part of the measuring beam 106 is not blocked and the illumination condition in which the center part thereof is blocked.

An electrical signal for acquiring a first tomographic image 151 is obtained in the illumination condition in which the center part of the measuring beam 106 is not blocked.

In the third step, the illumination condition varying unit 145 is used to obtain an electrical signal for acquiring a second tomographic image 152 in the illumination condition in which the center part of the measuring beam 106 is blocked.

In the fourth step, the electrical signal for acquiring the first tomographic image 151 and the electrical signal for acquiring the second tomographic image 152 which are different in amplitude from each other are weighted and added to each other through operation to adjust contrasts, thereby forming a third tomographic image 153.

Therefore, even when the first tomographic image 151 and the second tomographic image 152 are significantly different in contrast from each other, the electrical signal for acquiring the first tomographic image 151 and the electrical signal for acquiring the second tomographic image 152 are weighted and added to each other through operation, and the tomographic image whose contrast is high can be finally acquired.

(10) According to the optical tomographic imaging method in this embodiment, at least one of the first to fourth steps may be automatically performed. Therefore, the tomographic image can be automatically maintained at high contrast.

EXAMPLES

Hereinafter, examples of the present invention are described.

Example 1

In Example 1, an optical coherence tomographic imaging apparatus (OCT apparatus) to which the present invention is applied is described.

In this example, particularly, time domain OCT (TD-OCT) for acquiring a tomographic image of a retina of an eye is described.

The present invention may be applied to not only the TD-OCT but also a Fourier domain OCT (FD-OCT).

The schematic structure of the entire optical system of the OCT apparatus according to this example is described.

FIG. 1A is an explanatory view illustrating the schematic structure of the entire optical system of the OCT apparatus according to this example.

In FIG. 1A, an OCT apparatus 100 includes beam splitters 103-1 to 103-3, single-mode optical fibers 110-1 to 110-4, lenses 111-1 to 111-4 and 120-1 and 120-2, and reference minors 114-1 to 114-5. Reference numeral 105 denotes a reference beam, 106 denotes a measuring beam, 107 denotes an eye (object), and 108 denotes a return beam.

The OCT apparatus 100 further includes dispersion compensation glasses 115-1 to 115-3, acoustooptic modulators 116-1 and 116-2, motor-driven stages 117-1 and 117-2, an XY-scanner 119, a balanced detector 122, an amplifier 123, a filter 124, an A/D converter 128, a personal computer 125, a detector 138, and a variable neutral density filter (light intensity varying portion) 144. Reference numeral 126 denotes a cornea and 127 denotes a retina.

The OCT apparatus 100 further includes an illumination condition varying portion 145 which includes a circular aperture 145-1 and a ring aperture 145-2.

As illustrated in FIG. 1A, the entire OCT apparatus 100 according to this example serves as a Mach-Zehnder interference system.

In FIG. 1A, the beam emitted from the light source 101 is split into the reference beam 105 and the measuring beam 106 by the beam splitter 103-1.

The measuring beam 106 is reflected or scattered by the eye 107 which is an observation object, and returned as the return beam 108. The return beam 108 is split into a return beam (first return beam) 108-1 and a return beam (second return beam) 108-2 by a beam splitter 103-3. Of the return beams, the return beam 108-1 is combined with the reference beam 105 at the beam splitter 103-2.

After the reference beam 105 and the return beam 108-1 are combined with each other, a resultant beam is split by the beam splitter 103-2 to be made incident on the balanced detector 122 of the opto-electric conversion circuit.

The balanced detector 122 converts a light intensity into a voltage signal. A tomographic image of the eye 107 is formed based on the voltage signal.

Next, the light source 101 and its surroundings are described.

The light source 101 is a super luminescent diode (SLD) which is a typical low-coherent light source.

The wavelength of the light source is 830 nm, and the bandwidth thereof is 50 nm. The bandwidth is an important parameter affecting the resolution of an acquired tomographic image in an optical axis direction.

In this example, the SLD is selected regarding the type of the light source. Any light source capable of emitting a low-coherent beam may be used. For example, an amplified spontaneous emission (ASE) source may be used.

In view of the point that the eye is to be measured, a wavelength in the near infrared region is suitable. The wavelength affects a lateral resolution of the acquired tomographic image, and hence a desirable wavelength is as short as possible and is set to 830 nm in this example. Another wavelength may be selected depending on a measurement region of the observed object.

The beam emitted from the light source 101 is guided to a lens 111-1 through a single-mode optical fiber 110-1 and adjusted so as to become a parallel beam whose beam diameter is 4 mm.

Next, an optical path of the reference beam 105 is described.

The reference beam 105 obtained by splitting by the beam splitter 103-1 passes through the reference mirrors 114-1 to 114-5 in this order, to change a travelling direction. Then, the reference beam 105 is made incident on the balanced detector 122 by the beam splitter 103-2.

Of the dispersion compensation glasses 115-1 and 115-2, the length of the dispersion compensation glass 115-1 is expressed by L1 and desirably equal to two times the depth of a normal eye.

The dispersion compensation glass 115-1 is used for the reference beam 105 to compensate for dispersion when the measuring beam 106 goes to and comes back from the eye 107.

The length L1 is set to 46 mm which is twice the length 23 mm which is considered to be equal to an average eyeball diameter of Japanese people.

The motor-driven stages 117-1 can be moved in a direction indicated by the arrow to adjust or control the optical length of the reference beam 105.

Next, a method of modulating the reference beam 105 is described.

The acoustooptic modulators 116-1 and 116-2 are controlled by an acoustooptic modulator controller 116-3.

The two acoustooptic modulators 116-1 and 116-2 are used as optical frequency shifters.

Shift frequencies of the acoustooptic modulators 116-1 and 116-2 are +41 MHz and −40 MHz, and hence the frequency of the reference beam 105 is shifted by 1 MHz.

The dispersion compensation glass 115-2 is used for dispersion compensation of the lenses 120-1 and 120-2 for scanning the eye 107.

Next, the optical path of the measuring beam 106, which is a feature of the present invention, is described.

The measuring beam 106 obtained by splitting by the beam splitter 103-1 passes through the dispersion compensation glass 115-3, is reflected on the beam splitter 103-3, and passes through the variable neutral density filter 144, thereby obtaining the neutral density.

The variable neutral density filter 144 is provided to vary the intensity of the measuring beam 106 incident on the eye 107.

The variable neutral density filter 144 is electrically connected to the personal computer 125 and may be controlled thereby.

The dispersion compensation glass 115-3 is provided to compensate for dispersions of the acoustooptic modulators 116-1 and 116-2.

Then, when the measuring beam 106 passes through the circular aperture 145-1, the measuring beam 106 is formed into a circular beam shape.

The circular aperture 145-1 is provided as the illumination condition varying portion and can be exchanged for another aperture.

A function of the circular aperture 145-1 or the illumination condition varying portion is a feature of the present invention and described in detail later.

Then, the measuring beam 106 is incident on a mirror of the XY-scanner 119.

For simplification, the XY-scanner 119 is illustrated as a single mirror. However, two mirrors, that is, an X-scanning mirror and a Y-scanning mirror are actually provided close to each other to raster-scan the retina 127 in the direction perpendicular to the optical axis.

The center of the measuring beam 106 is aligned with the center of rotation of the mirror of the XY-scanner 119.

The lenses 120-1 and 120-2 correspond to an optical system for scanning the retina 127 and has a function for scanning the retina 127 with the measuring beam 106 with the vicinity of the cornea 126 as a pivot. The focal length of each of the lenses 120-1 and 120-2 is 50 mm.

When the measuring beam 106 is incident on the eye 107, the measuring beam 106 becomes the return beam 108 because of reflection or scattering from the retina 127.

The return beam 108 is split into the return beam (first return beam) 108-1 and the return beam (second return beam) 108-2 by the beam splitter 103-3. The second return beam 108-2 passes through the beam splitter 103-1 and is guided to the detector 138.

The detector 138 to be used is, for example, an avalanche photo diode (APD) which is a high-speed high-sensitivity optical sensor.

The first return beam 108-1 is guided to the balanced detector 122. The motor-driven stage 117-2 can be moved in a direction indicated by the arrow to adjust or control the position of the associated lens 120-2. In the case where the position of the lens 120-2 is adjusted by the motor-driven stage 117-2, even when the eye 107 of a subject has a refraction aberration, the measuring beam 106 may be focused on the retina 127 to acquire the OCT image by the OCT apparatus 100.

Next, a measurement system of the OCT apparatus according to this example is described.

The OCT apparatus 100 can acquire a tomographic image (OCT image) based on the intensity of the interference signal obtained by the Mach-Zehnder interference system.

The measurement system is described. The return beam 108 which is light reflected or scattered on the retina 127 is split into the return beam 108-1 and the return beam 108-2 by the beam splitter 103-3.

Of the split return beams, the return beam 108-1 is split by the beam splitter 103-2. The reference beam 105 is also split by the beam splitter 103-2.

The reference beam 105 and the return beam 108-1 are adjusted to be combined after the beam splitter 103-2.

Then, the reference beam 105 and the return beam 108-1 are condensed by the lenses 111-2 and 111-3 and guided to the balanced detector 122 through the optical fibers 110-2 and 110-3. The intensity of light obtained by combining the reference beam 105 and the return beam 108-1 is converted into a voltage signal.

The obtained voltage signal is amplified by the amplifier 123. A necessary frequency component is extracted from the voltage signal by the filter 124. Then, the voltage signal is converted into a digital value by the A/D converter 128, and demodulated and data-processed by the personal computer 125 to form a tomographic image.

As described above, the reference beam 105 is frequency-shifted by 1 MHz. Therefore, the obtained voltage signal is a beat signal of 1 MHz. The return beam 108-1 is normally very weak but the reference beam 105 is large, and hence detection sensitivity may be increased.

The filter 124 to be used is a band-pass filter of 1 MHz. An unnecessary frequency component is cut to detect the beat signal with high sensitivity.

The second return beam 108-2 obtained by splitting by the beam splitter 103-3 described above passes through the beam splitter 103-1, is condensed by the lens 111-4, and is guided to the detector 138 through the optical fiber 110-4.

The detector 138 is electrically connected to the personal computer 125 through the A/D converter 128. As in the case of the interference signal, the intensity of the return beam 108-2 may be recorded and displayed.

A signal obtained by the detector 138 is an intensity signal of the return beam 108-2 reflected or scattered on the retina 127. The signal is different from the interference signal to have no depth resolution.

Next, the optical tomographic imaging method using the optical tomographic imaging apparatus (OCT apparatus) according to this example is described.

In the OCT apparatus 100, when the motor-driven stage 117-2 and the XY-scanner 119 are controlled, a tomographic image of a desirable region of the retina 127 can be acquired (FIG. 1A).

A method of acquiring the tomographic image of the retina 127 (plane parallel to optical axis) is described with reference to FIGS. 2A to 2C.

Figure 2A:
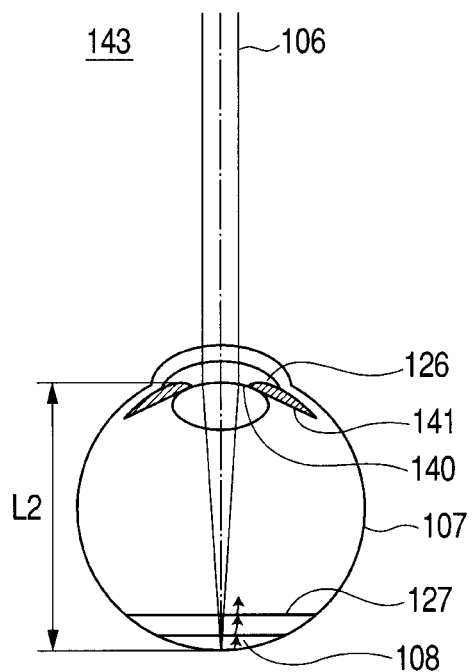
FIGS. 2A, 2B, and 2C are explanatory views illustrating a tomographic imaging method using the OCT apparatus according to Example 1 of the present invention.

FIG. 2A is a schematic view illustrating the eye 107 showing an observation state (143) by the OCT apparatus 100.

As illustrated in FIG. 2A, when the measuring beam 106 is incident on the retina 127 through the cornea 126, the measuring beam 106 becomes the return beams 108 because of reflection and scattering at various positions. The return beams 108 with time delays at the respective positions reach the balanced detector 122.

In this example, the bandwidth of the light source 101 is wide and the coherence length thereof is short. Therefore, only when the optical path length of the reference beam is equal to the optical path length of the measuring beam, the interference signal may be detected by the balanced detector 122. As described above, the frequency of the reference beam 105 is shifted relative to that of the measuring beam 106 by 1 MHz, and hence the interference signal is a beat signal of 1 MHz.

Figure 2B:
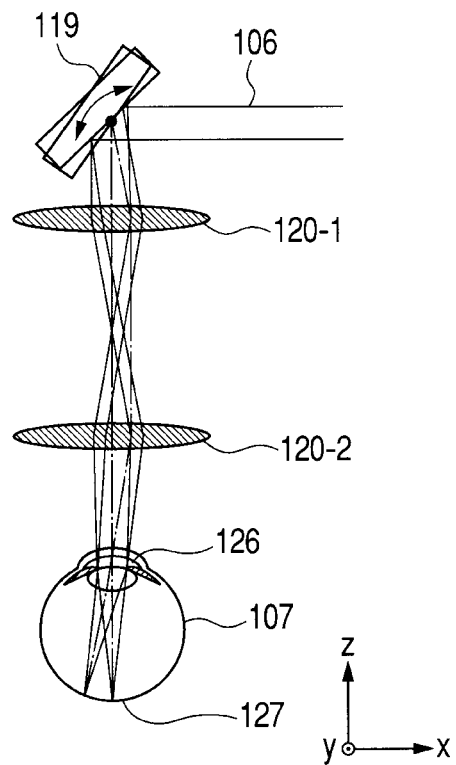
Figure 2C:
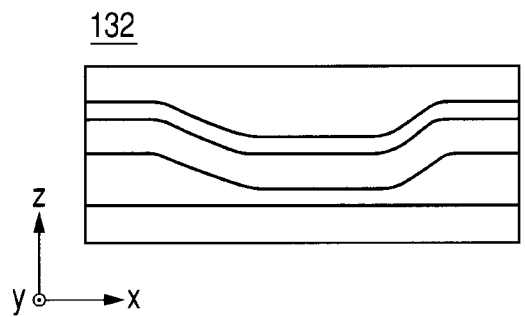

As illustrated in FIG. 2B, when interference signals are detected while the XY-scanner 119 is driven in an X-axis direction, each of the interference signals becomes a signal having X-axis position information. When amplitudes of the interference signals are squared and demodulated, an intensity distribution of the return beam 108 in the X-axis direction on an arbitrary XY-plane is acquired.

When the same operation is repeated while the optical path length of the reference beam is adjusted using the motor-driven stage 117-1, a two-dimensional intensity distribution of the return beam 108 on an XZ-plane is acquired. The intensity distribution corresponds to a tomographic image 132 (FIG. 2C).

As described above, the tomographic image 132 is acquired by arranging the intensities of the interference signals in an array. For example, each of the intensities of the interference signals is displayed according to the gray scale. In this example, only boundaries of the obtained tomographic image are enhanced for display.

Next, a tomographic image constructing method using the OCT apparatus with the feature of the present invention is described with reference to FIGS. 3A and 3B.

FIGS. 3A and 3B are explanatory views illustrating a measurement optical system of the OCT apparatus 100.

FIG. 3A illustrates a case where a circular aperture 145-1 is used as the illumination condition varying portion as described above.

In contrast to this, FIG. 3B illustrates a case where a ring aperture 145-2 instead of the circular aperture 145-1 is used as the illumination condition varying portion.

The case where the circular aperture 145-1 is used as the illumination condition varying portion as illustrated in FIG. 3A is described.

The measuring beam 106 is reduced in intensity by a variable neutral density filter 144 and formed into a circular beam shape by the circular aperture 145-1, thereby entering the retina 127.

The beam shape is illustrated in FIG. 3A. The intensity of the measuring beam 106 is adjusted to a value equal to or smaller than 700 μW in view of safety.

However, in view of S/N ratio of the balanced detector 122, the intensity of the measuring beam 106 is desirably a large value.

The intensity of the measuring beam 106 may be measured in advance or measured in real time (not shown).

Figure 4A:
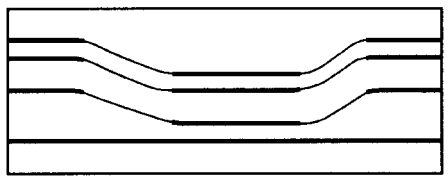

FIG. 4A is a schematic view illustrating a case where a tomographic image acquired in this condition is a first tomographic image 151.

FIG. 4A schematically illustrates only boundaries of an image acquired by adapting the intensities of the amplitudes of the electrical signals obtained by the balance detector 122 to the gray scale. The thickness of each of the boundaries indicates a contrast of the tomographic image.

As is apparent from FIG. 4A, a contrast of regions substantially perpendicular to the optical axis of the measuring beam 106 is high and a contrast of regions which are not substantially perpendicular thereto is relatively low.

For description, a contrast difference is exaggerated.

Next, the case where the ring aperture 145-2 instead of the circular aperture 145-1 is used as the illumination condition varying portion as illustrated in FIG. 3B is described.

The ring aperture 145-2 is provided for so-called annular illumination and is used to make the measuring beam 106 obliquely incident on the retina 127 in this example.

The measuring beam 106 is reduced in intensity by the variable neutral density filter 144 and formed into a ring beam shape by the ring aperture 145-2, thereby entering the retina 127.

The beam shape is illustrated in FIG. 3B.

The intensity of the measuring beam 106 is adjusted to a value equal to or smaller than 700 μW in view of safety. In this example, the intensity of the measuring beam 106 is reduced by the ring aperture 145-2, and hence the measuring beam 106 incident on the eye 107 is adjusted by the variable neutral density filter 144 to set the intensity to approximately 700 μW again.

Further, in view of S/N ratio of the balanced detector 122, the intensity of the measuring beam 106 is desirably a large value.

Figure 4B:
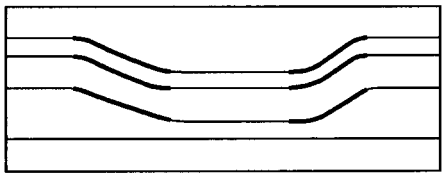

FIG. 4B is a schematic view illustrating a case where a tomographic image acquired in this condition is a second tomographic image 152.

FIG. 4B schematically illustrates only boundaries in the case where the intensity of the return beam 108 is adapted to the gray scale.

The thickness of each of the boundaries indicates the contrast of the tomographic image.

As is apparent from FIG. 4B, a contrast of a region which is not blocked by the ring aperture 145-2 is high and a contrast of a region which is blocked by the ring aperture 145-2 is relatively low.

For description, a contrast difference is exaggerated.

As compared with the case where the first tomographic image is acquired, the amplitude of the electrical signal obtained by the balanced detector 122 is small. Therefore, it is necessary to suitably set the amplification of the A/D converter 128 by an amplification control unit.

Next, a method of constructing a third tomographic image based on the first tomographic image and the second tomographic image is described.

The first tomographic image and the second tomographic image are fundamentally added to each other.

However, the amplitudes of the electrical signals obtained by the balanced detector 122 of the first tomographic image and the second tomographic image are different from each other. Therefore, the electrical signals are suitably weighted and added to each other to obtain an excellent contrast.

Figure 4C:
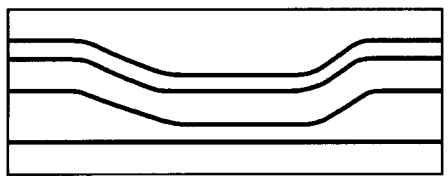
Figure 4D:
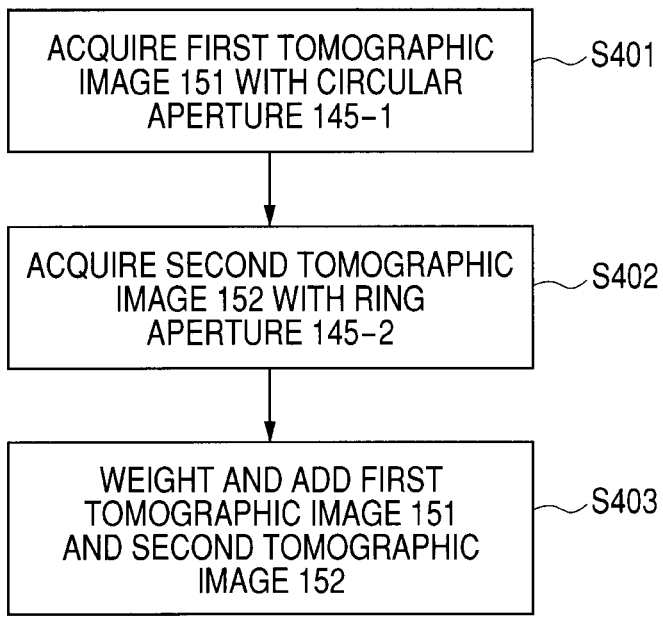

To be more specific, according to this constructing method, for example, steps illustrated in FIG. 4D are successively conducted. Alternatively, it may be suitable to return to a certain step to conduct it. The following steps may be performed automatically using a computer.

In FIG. 4D, 'S401' indicates a step of acquiring the first tomographic image 151 using the circular aperture 145-1. In this case, a first measuring beam having an illumination condition in which a center part thereof is not blocked is incident on a fundus at a first light intensity. The first tomographic image is acquired based on the return beam of the first measuring beam from the fundus. Next, 'S402' indicates a step of acquiring the second tomographic image 152 using the ring aperture 145-2 instead of the circular aperture 145-1. In this case, the first measuring beam is changed by the illumination condition varying portion to a second measuring beam having an illumination condition in which a center part of the second measuring beam is blocked. The light intensity of the second measuring beam is adjusted by the light intensity varying portion to a second light intensity such that the second measuring beam is incident on the fundus at the first light intensity. The second measuring beam is incident on the fundus at the second light intensity. The second tomographic image is acquired based on the return beam of the second measuring beam from the fundus. Next, 'S403' indicates a step of weighting and adding the first tomographic image 151 and the second tomographic image 152 to acquire a third tomographic mage 153. The weighting is adjusted such that the contrast of the entire third tomographic image 153 is excellent.

FIG. 4C is a schematic view illustrating the acquired third tomographic image.

As is observed from FIG. 4C, an excellent contrast is achieved.

In order that the measuring beam 106 is obliquely incident on the retina 127, for example, a quadrupole aperture (not shown) instead of the ring aperture 145-2 may be used as an aperture having multiple openings.

Figure 4E:
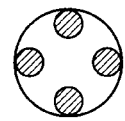

FIG. 4E illustrates a quadrupole aperture beam shape.

With the quadrupole aperture, the same effect as that of the ring aperture is obtained. Thus, the ring aperture and the quadrupole aperture may be separately used according to circumstances.

Example 2

In Example 2, a structural example in which optical fibers are provided for any optical paths described in Example 1 is described.

Figure 1B:
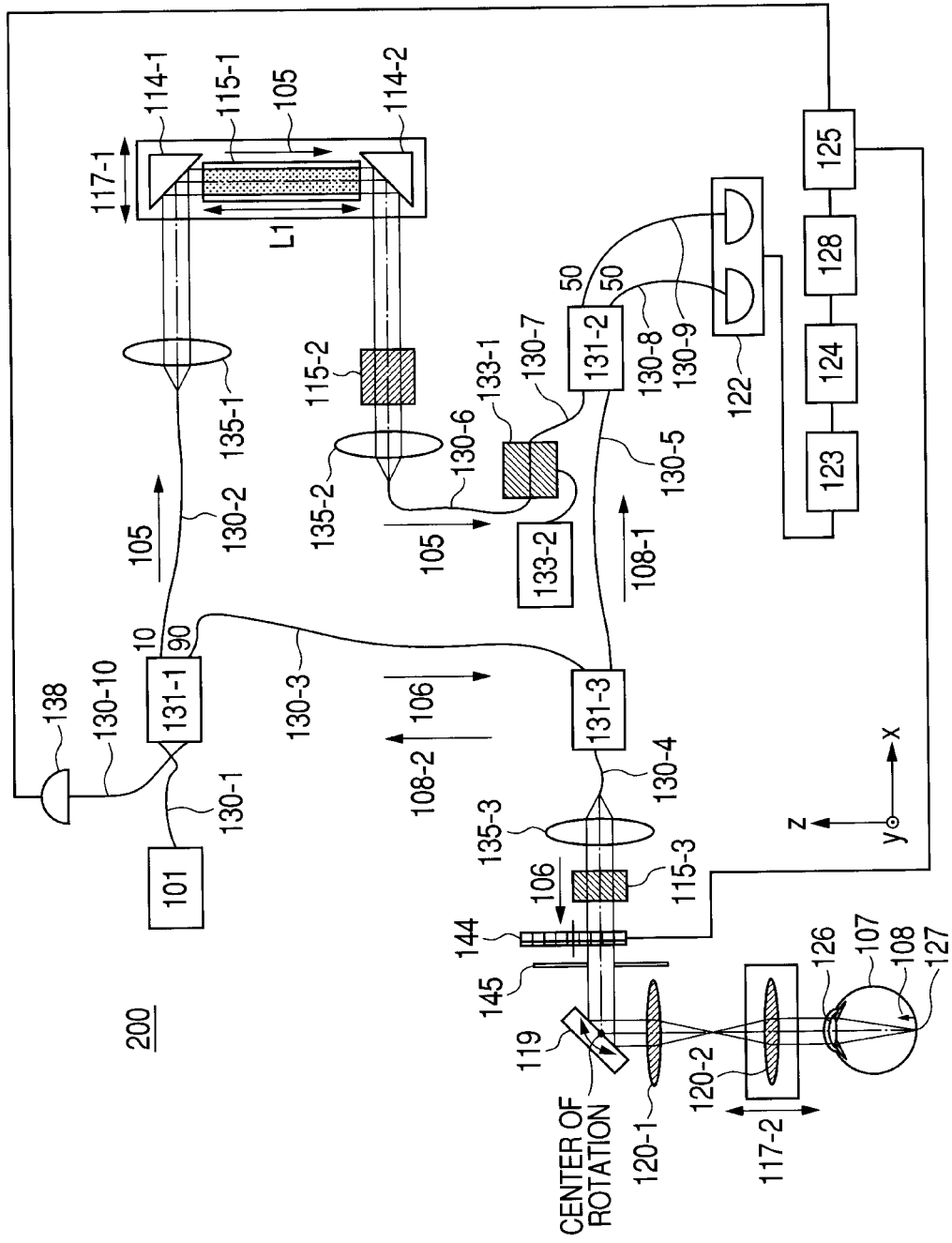

FIG. 1B is an explanatory view illustrating a schematic structure of the entire optical system of an OCT apparatus according to this example.

In FIG. 1B, constituent elements which are identical to or correspond to the constituent elements in Example 1 as described in FIG. 1A are expressed by the same reference numerals and symbols, and thus the duplicated description is omitted. In FIG. 1B, an OCT apparatus 200 includes single-mode optical fibers 130-1 to 130-10, and optical couplers 130-1 to 131-3.

In this example, the OCT apparatus 200 is used as an apparatus for acquiring a tomographic image of the retina 127 of the eye 107 to be inspected.

In this example, optical fibers are used for constructing parts of the optical system to reduce a size of the OCT apparatus. Except for the use of the optical fibers, the OCT apparatus according to this example has a structure which is not different from the fundamental structure of Example 1.

The structure of the optical system of the OCT apparatus according to this example is described.

The structure of the OCT apparatus 200 is briefly described. As illustrated in FIG. 1B, the OCT apparatus 200 according to this example serves as a Mach-Zehnder interference system.

In FIG. 1B, the measuring beam 106 is reflected or scattered by the eye 107 which is an observation object, and returned as the return beam 108-1. Then, the return beam 108-1 is combined with the reference beam 105 by the optical coupler 131-2.

After the reference beam 105 and the return beam 108-1 are combined with each other, a resultant beam is split to be made incident on the balanced detector 122. A tomographic image of the eye 107 is constructed based on light intensities obtained by the balanced detector 122.

Next, the light source 101 and its surroundings are described.

The light source 101 itself is the same as in Example 1. The beam emitted from the light source 101 is guided to the optical coupler 131-1 through the single-mode optical fiber 130-1, and split into the measuring beam 106 and the reference beam 105 at an intensity ratio of 90:10.

Next, an optical path of the reference beam 105 is described.

The reference beam 105 obtained by splitting by the optical coupler 131-1 is guided to a lens 135-1 through the single-mode optical fiber 130-2. Therefore, the reference beam 105 is adjusted so as to become a parallel beam whose beam diameter is 4 mm.

The motor-driven stages 117-1, the associated mirrors 114-1 and 114-2, and the dispersion compensation glass 115-1 are the same as in Example 1, and hence the description thereof is omitted.

The reference beam 105 passes through the dispersion compensation glass 115-2 and then is guided to the single-mode optical fiber 130-6 by a lens 135-2.

After that, the reference beam 105 passes through an acoustooptic modulator 133-1 and a single-mode optical fiber 130-7 and enters the optical coupler 131-2. The acoustooptic modulator 133-1 is used for optical fibers, and may perform a frequency shift of 1 MHz by a controller 133-2.

Therefore, the obtained reference beam 105 in this example is the same as that of Example 1.

Next, an optical path for the measuring beam 106 featuring of the present invention is described.

The measuring beam 106 obtained by splitting by the optical coupler 131-1 passes through the single-mode optical fiber 130-3 and enters the optical coupler 131-3.

After that, the measuring beam 106 is guided to a lens 135-3 through the single-mode optical fiber 130-4. Therefore, the measuring beam 106 is adjusted so as to become a parallel beam whose beam diameter is 4 mm.

The measuring beam 106 passes through the dispersion compensation glass 115-3 and then passes through the variable neutral density filter 144, thereby obtaining a neutral density. The variable neutral density filter 144 is electrically connected to the personal computer 125 and may be controlled thereby.

Then, when the measuring beam 106 passes through the circular aperture 145-1, the measuring beam 106 is formed into a desired beam shape.

The circular aperture 145-1 is provided as an illumination condition varying portion and can be exchanged for another aperture.

Then, the measuring beam 106 is incident on a mirror of the XY-scanner 119.

The optical system between the variable neutral density filter 144 and the eye 107 is the same as that of Example 1, and hence the detailed description is omitted.

The dispersion compensation glass 115-3 is provided to compensate for dispersion of the acoustooptic modulator 133-1.

In this example, the measuring beam 106 passes through the dispersion compensation glass 115-3 in forward and backward directions, and hence the thickness of the dispersion compensation glass 115-3 is set to half the glass thickness of the acoustooptic modulator 133-1. When the measuring beam 106 is incident on the eye 107, the measuring beam 106 becomes the return beam 108 because of reflection or scattering from the retina 127.

Then, the return beam 108 is guided to the optical coupler 131-2 through the optical coupler 131-3.

Next, a measurement system of the OCT apparatus according to this example is described.

The OCT apparatus 200 can acquire a tomographic image (OCT image) based on the intensity of an interference signal obtained by the Mach-Zehnder interference system.

The measurement system is described. The first return beam 108-1 of the return beam 108 which is light reflected or scattered on the retina 127 is combined with the reference beam 105 by the optical coupler 131-2, and a resultant beam is split into two beams at an intensity ratio of 50:50.

Then, the beams are guided to the balanced detector 122 through the single-mode optical fibers 130-8 and 130-9. An intensity of light obtained by combining the reference beam 105 and the return beam 108-1 is converted into a voltage signal.

The obtained voltage signal is amplified by the amplifier 123. A necessary frequency component is extracted from the voltage signal by the filter 124. Then, the voltage signal is converted into a digital value by the A/D converter 128, and demodulated and data-processed by the personal computer 125 to form the tomographic image.

The second return beam 108-2 of the return beam 108 described above is guided to the detector 138 through the optical coupler 131-1 and the optical fiber 130-10. The detector 138 is electrically connected to the personal computer 125 as in the case of the interference signal. The intensity of the return beam 108-2 may be recorded and displayed. Further, a signal obtained by the detector 138 is an intensity signal of the return beam 108-2 reflected or scattered on the retina 127, and therefore the signal is different from the interference signal to have no depth resolution.

The tomographic image acquiring method featuring the present invention is the same as that of Example 1, and hence the detailed description is omitted.

The tomographic image constructing method is the same as that of Example 1, and hence the detailed description is omitted.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-177108, filed Jul. 7, 2008, which is hereby incorporated by reference herein in its entirety.

What is claimed is:

1. An imaging apparatus comprising:
a varying unit configured to vary a condition of a measuring beam that irradiates a retina of a subject eye via a scanning unit, wherein the scanning unit scans the measuring beam on the retina with a vicinity of a cornea of the subject eye as a pivot; and
a control unit configured to control said varying unit to vary the condition between a first condition, in which a radially center part of the measuring beam is not blocked, and a second condition, in which the radially center part of the measuring beam is blocked.

2. An imaging apparatus according to claim 1, further comprising an acquiring unit configured to acquire a first image of the retina irradiated by the measuring beam in the first condition and a second image of the retina irradiated by the measuring beam in the second condition.

3. An imaging apparatus according to claim 1, further comprising an image forming unit configured to compose a first image of the retina irradiated by the measuring beam in the first condition and a second image of the retina irradiated by the measuring beam in the second condition.

4. An imaging apparatus according to claim 1, wherein said control unit controls said scanning unit in the second condition.

5. An imaging apparatus according to claim 2, wherein said acquiring unit acquires a first tomographic image, as the first image, based on a return beam from the retina irradiated by the measuring beam in the first condition and a reference beam corresponding to the measuring beam, and
wherein said acquiring unit acquires a second tomograhic image, as the second image, based on a return beam from the retina irradiated by the measuring beam in the second condition and a reference beam corresponding to the measuring beam.

6. An imaging method comprising:
varying a condition of a measuring beam that irradiates a retina of a subject eye via a scanning unit, wherein the scanning unit scans the measuring beam on the retina with a vicinity of a cornea of the subject eye as a pivot; and
controlling performance of said varying to vary the condition between a first condition, in which a radially center part of the measuring beam is not blocked, and a second condition, in which the radially center part of the measuring beam is blocked.

7. An imaging method according to claim 6, further comprising acquiring a first image of the retina irradiated by the measuring beam in the first condition and a second image of the retina irradiated by the measuring beam in the second condition.

8. An method according to claim 6, further comprising composing a first image of the retina irradiated by the measuring beam in the first condition and a second image of the retina irradiated by the measuring beam in the second condition.

9. An imaging method according to claim 6, further comprising:
controlling said scanning unit in the second condition, causing the scanning unit to scan the measuring beam on the subject eye.

10. A non-transitory computer-readable storage medium, storing, in executable form, a program for causing a computer to perform a method according to claim 6.

11. An imaging method according to claim 7, wherein said acquiring is performed in such manner as to acquire a first tomographic image, as the first image, based on a return beam from the retina irradiated by the measuring beam in the first condition and a reference beam corresponding to the measuring beam, and
wherein said acquiring is performed so as to acquire a second tomograhic image, as the second image, based on a return beam from the retina irradiated by the measuring beam in the second condition and a reference beam corresponding to the measuring beam.

12. An ophthalmologic apparatus in which a tomographic image of a subject eye is acquired based on a return beam of a measuring beam, which is reflected or scattered by the subject eye irradiated with the measuring beam via a scanning unit, and a reference beam corresponding to the measuring beam, wherein the scanning unit scans the measuring beam on the subject eye, said ophthalmologic apparatus comprising:
a light source;
a splitting unit for splitting a beam from said light source into the measuring beam and the reference beam;
a varying unit configured to vary an intensity of the measuring beam, and a condition of the measuring beam, said varying unit being provided on an optical path for guiding the measuring beam to the subject eye and provided between said splitting unit and said scanning unit; and
a control unit configured to control said varying unit to vary the condition between a first condition, in which a radially center part of the measuring beam is not blocked, and a second condition, in which the radially center part of the measuring beam is blocked, and to adjust the intensity of the measuring beam on the subject eye to a predetermined intensity.

13. An ophthalmologic apparatus according to claim 12, wherein the predetermined intensity is about 700 μW.

14. An ophthalmologic apparatus according to claim 12, wherein said control unit controls said varying unit so as to automatically maintain a constant intensity of the measuring beam on the subject eye.

15. An ophthalmologic apparatus according to claim 12, wherein said varying unit comprises a variable neutral density filter.

16. An ophthalmologic apparatus according to claim 12, wherein said control unit controls said varying unit according to a change in an illumination condition of the measuring beam with respect to the subject eye.

17. An ophthalmologic apparatus according to claim 12,
wherein said varying unit comprises a variable neutral density filter, and
wherein said varying unit is provided on an optical path for guiding the measuring beam to the subject eye and provided between said splitting unit and said scanning unit.

18. An ophthalmologic apparatus according to claim 12, wherein the scanning unit scans the measuring beam on a retina of the subject eye with a vicinity of a cornea of the subject eye as a pivot.

19. An ophthalmologic method in which a tomographic image of a subject eye is acquired based on a return beam of a measuring beam, which is reflected or scattered by the subject eye irradiated with the measuring beam via a scanning unit, and a reference beam corresponding to the measuring beam, wherein the scanning unit scans the measuring beam on the subject eye, said ophthalmologic method comprising:
varying, by a varying unit, an intensity of the measuring beam and a condition of the measuring beam; and
controlling the varying unit to vary the condition between a first condition, in which a radially center part of the measuring beam is not blocked, and a second condition, in which the radially center part of the measuring beam is blocked, and to adjust an intensity of the measuring beam on the subject eye to a predetermined intensity.

20. An ophthalmologic method according to claim 19, wherein the predetermined intensity is about 700 μW.

21. An ophthalmologic method according to claim 19, further comprising controlling the varying unit so as to automatically maintain a constant intensity of the measuring beam on the subject eye.

22. A non-transitory computer-readable storage medium, storing, in executable form, a program for causing a computer to perform a method according to claim 19.

23. An ophthalmologic method according to claim 19, wherein the scanning unit scans the measuring beam on a retina of the subject eye with a vicinity of a cornea of the subject eye as a pivot.

* * * * *